United States Patent
Robbins et al.

(10) Patent No.: US 10,709,646 B2
(45) Date of Patent: Jul. 14, 2020

(54) ORAL CARE WHITENING COMPOSITIONS

(71) Applicant: Colgate-Palmolive Company, New York, NY (US)

(72) Inventors: Kyle Robbins, Toms River, NJ (US); Stacey Lavender, Chesterfield, NJ (US); Jason Nesta, Cedar Knolls, NJ (US); Guofeng Xu, Plainsboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/972,649

(22) Filed: Dec. 17, 2015

(65) Prior Publication Data

US 2017/0172866 A1 Jun. 22, 2017

(51) Int. Cl.

| | |
|---|---|
| *A61K 8/23* | (2006.01) |
| *A61Q 11/00* | (2006.01) |
| *A61K 8/04* | (2006.01) |
| *A61K 8/891* | (2006.01) |
| *A61K 8/81* | (2006.01) |
| *A61K 8/22* | (2006.01) |
| *A61Q 11/02* | (2006.01) |
| *A61K 8/86* | (2006.01) |

(52) U.S. Cl.
CPC ............... *A61K 8/23* (2013.01); *A61K 8/042* (2013.01); *A61K 8/22* (2013.01); *A61K 8/8176* (2013.01); *A61K 8/8182* (2013.01); *A61K 8/86* (2013.01); *A61K 8/891* (2013.01); *A61Q 11/00* (2013.01); *A61Q 11/02* (2013.01); *A61K 2800/31* (2013.01); *A61K 2800/49* (2013.01); *A61K 2800/592* (2013.01)

(58) Field of Classification Search
USPC .......................................................... 424/49
See application file for complete search history.

(56) References Cited

U.S. PATENT DOCUMENTS

| 4,971,782 | A | * | 11/1990 | Rudy ..................... A61K 8/11 424/53 |
| 8,815,215 | B2 | * | 8/2014 | Prencipe .............. A61C 19/066 424/53 |
| 2002/0187108 | A1 | | 12/2002 | Rajaiah et al. |
| 2005/0069502 | A1 | | 3/2005 | Chopra et al. |
| 2005/0137110 | A1 | | 6/2005 | Scott et al. |
| 2006/0147394 | A1 | * | 7/2006 | Shastry .................. A61K 8/22 424/49 |
| 2012/0328535 | A1 | * | 12/2012 | Zaidel ..................... A61K 8/22 424/53 |
| 2014/0314693 | A1 | | 10/2014 | Boyd et al. |
| 2014/0377194 | A1 | * | 12/2014 | Strand .................... A61Q 11/00 424/57 |
| 2015/0037266 | A1 | | 2/2015 | Boyd et al. |
| 2015/0366778 | A1 | | 12/2015 | Boyd et al. |

FOREIGN PATENT DOCUMENTS

| WO | WO 2001/001939 | 1/2001 |
| WO | WO 2005/018593 | 3/2005 |
| WO | WO 2013/095369 | 6/2013 |

OTHER PUBLICATIONS

International Search Report and Written Opinion of the International Searching Authority in International Application No. PCT/US2016/066070, dated Feb. 16, 2017.

* cited by examiner

*Primary Examiner* — Walter E Webb

(57) ABSTRACT

Described herein are oral care whitening compositions comprising a non-aqueous phase comprising a peroxysulfate whitening agent, a hydrophobic base and at least one hydrophilic polymer, and optionally an aqueous phase comprising at least one hydrophilic polymer. Methods of making and using these compositions are also described herein.

15 Claims, No Drawings

ORAL CARE WHITENING COMPOSITIONS

BACKGROUND

Products that are presently available to whiten teeth include a variety of different ingredients, but the primary active ingredient is a peroxide source such as hydrogen peroxide. In high concentrations, hydrogen peroxide can be irritating to the teeth and/or gums. In addition, hydrogen peroxide is an unstable molecule that is prone to decomposition, especially in aqueous environments. This presents difficulties in terms of formulating a stable composition for consumer consumption. Thus, alternative oxidizing agents with improved stability are desired.

Peroxysulfuric acid, and its salts, the peroxysulfates, are powerful oxidizing and stain removing agents. They are currently used for a variety of industrial and consumer purposes, including swimming pool treatment and denture cleaning. The most common peroxymonosulfate oxidizing agent is potassium peroxymonosulfate, commonly referred to as MPS.

Potassium monoperoxysulfate has seen limited use in dental whitening compositions because of its instability in aqueous solution, especially in aqueous solution near or above neutral pH While potassium monoperoxysulfate is somewhat stable in aqueous solutions at acidic pH, it is more stable either as a solid or in an anhydrous formulation, and it is most active as an oxidizing agent (and tooth whitening agent) in an aqueous solution at pH 5-8. Anhydrous formulations typically include primarily hydrophobic polymers in a hydrophobic base. While these can achieve good stability, they often show poor dispensing characteristics. Thus, there has been difficulty formulating monoperoxysulfate based compositions with good rheological properties (dispensing characteristics) and good stability and whitening efficacy.

Improved tooth whitening formulations are desired which combine the relative stability of monoperoxysulfate salts in an anhydrous environment, with effective whitening and dispensing characteristics.

SUMMARY

In some embodiments, the present disclosure provides a single-phase non-aqueous oral whitening composition comprising: a hydrophobic base, one or more hydrophilic polymers, and a peroxysulfate whitening agent.

In some embodiments, the present disclosure provides a dual-phase dental whitening composition, comprising a first non-aqueous phase comprising a hydrophobic base, one or more hydrophilic polymers, and a peroxysulfate whitening agent, and a second aqueous phase, comprising a hydrophilic polymer.

In some embodiments, the present disclosure provides methods of whitening a tooth comprising applying any of the compositions described herein to a tooth of a mammal.

Further areas of applicability of the present invention will become apparent from the detailed description and examples provided hereinafter. It should be understood that the detailed description and specific examples, while providing specific embodiments of the invention, are intended for illustration only and should in no way limit the scope of the invention.

DETAILED DESCRIPTION

The present disclosure provides a dental whitening composition comprising at least a non-aqueous phase comprising a hydrophobic base, one or more hydrophilic polymers, and a peroxysulfate whitening agent, and optionally a second aqueous phase comprising one or more hydrophilic polymers.

Thus, in some embodiments, the composition is a single phase non-aqueous composition, while in other embodiments, the composition is a dual-phase composition comprising a non-aqueous phase and an aqueous phase.

In some embodiments, at least one phase of the composition is a viscous liquid, preferably a gel, which maintains its consistency during storage enabling the product to be painted on the tooth surface with a soft applicator pen or brush. In some embodiments, wherein the invention is a dual-phase composition, both phases are viscous liquids or gels. Where the composition is a dual-phase composition, the two phases are mixed at the time of application.

The present disclosure provides portable viscous liquid or gel tooth whiteners that can be applied to the teeth as a coated layer conveniently painted onto the tooth enamel surface. Upon application to the teeth, the applied whitening composition forms an adherent layer of whitening product that has the capacity to exert a whitening effect over an extended period of time, e.g., from about 5 minutes to about 12 hours. The viscosity of the composition allows the applied layer to adhere to the tooth surface where the whitening agent can exert its effect over an extended period of time.

The non-aqueous phase of the composition is substantially anhydrous, meaning that no water is added. The phase may contain trace levels of water from ingredients or from product manufacture; however, such trace levels are insubstantial and do not interfere with the hydrophobic character of the phase.

The peroxysulfate whitening agent can be any suitable salt of peroxysulfuric acid, including peroxymonosulfates and peroxydisulfates, such as potassium peroxymonosulfate and sodium peroxymonosulfate, or a mixture of such salts. An example of a particularly useful agent is a triple salt mixture comprising potassium hydrogen peroxymonosulfate, potassium hydrogen sulfate, and potassium sulfate. Optionally, such a mixture may further include potassium peroxydilsulfate. An example of such a commercially available mixture is "Oxone", which is the trade name of a mixture sold by DuPont, Oxone consists of 43% potassium hydrogen peroxymonosulfate, 23% potassium hydrogen sulfate, 29% potassium sulfate, 3% potassium peroxidisulfate, and 2% magnesium carbonate. Mixtures of these potassium reagents are usually available as a powder or solid which, when dissolved in water, typically forms a highly acidic solution (e.g., pH 1-4) which is fairly stable on storage. For example, a 1-3% solution of Oxone has a pH of 2.0-2.3. Above pH 6, however, these mixtures are strong oxidizing agents which readily decomposes to release reactive oxygen species. Many sources uses the terms "potassium hydrogen peroxymonosulfate" or "potassium peroxymonosulfate" to refer to the above triple salt mixture that comprises Oxone ($2KHSO_5$—$KHSO_4$—$K_2SO_4$). As used herein, however, the terms "potassium hydrogen peroxymonosulfate," "potassium peroxymonosulfate," and "MPS" refer to the individual chemical species with the formula $KHSO_5$.

The non-aqueous phase of the composition comprises the peroxysulfate whitening agent in an amount such that, for a single-phase composition, the amount is effective to whiten the teeth, while for a dual-phase composition, the amount is effective to whiten the teeth after admixture with the aqueous-phase of the composition. A suitable effective amount can be from 0.11 to 40 wt % of the total composition (both phases together if dual phase). For example, an effective amount may be from 1 to 40 wt % of the total composition, or 1 to 20 wt %, or 1 to 15 wt %, or 1 to 10 wt % or 1 to 5 wt %, or 5 to 10 wt %, or about 1%, or about 5% or about 10%. In a particular embodiment, the single-phase composition comprises from 0.5 to 15% peroxysulfate whitening agent, e.g., 0.5-5%, or 0.5-2%, or about 1% In another particular embodiment, the single-phase composition comprises from 5% to 15% peroxysulfate whitening agent, e.g., 7.5-12.5%, or 8-12%, or about 10%. In another particular embodiment, the dual-phase composition comprises, by weight of the combined phases, from 0.5-20% peroxysulfate whitening agent, e.g., from 1-10%, or 2.5-7.5% or about 5%. In another particular embodiment, the dual-phase composition comprises, by weight of the combined phases, from 0.5 to 15% peroxysulfate whitening agent, e.g., 0.5-5%, or 0.5-2%, or about 1%.

The hydrophobic base comprises at least one silicone compound selected from silicone polymers, silicone adhesives, silicone gums, silicone waxes, silicone elastomers, silicone fluids, silicone resins, silicone powders, and mixtures thereof. The term "hydrophobic" or "water-insoluble" as applied to polymers and as employed herein refers to an organic polymer which is substantially non-aqueous having a water solubility of less than one gram per 100 grams of water at 25° C. Such silicone compounds serve to both create a stable hydrophobic environment for the whitening agent, and to help impart the desired gel-like consistency to the composition.

Gels comprising a silicone compound, a porous cross-linked polymer, and optionally a hydrophilic organic polymer are disclosed in U.S. Pat. No. 8,568,695, the contents of which are hereby incorporated herein by reference in its entirety.

In some embodiments, the hydrophobic base comprises "siloxane" polymers, which are also generally known in the art as "silicone" polymers. In various embodiments, a preferred silicone-based hydrophobic polymer is a polyorganosiloxane, in particular polydimethylsiloxane (generally known as dimethicone).

In some embodiments, the hydrophobic base comprises a silicone gum (e.g., a polysiloxane gum). Silicone gums useful herein include high molecular weight polydiorganosiloxanes having a viscosity, at 25° C., of 500,000 cSt up to 50,000,000 cSt (centiStokes). Such silicone gums include those polydiorganosiloxanes with a weight average molecular weight of greater than 500,000. The polysiloxane gums for use herein can be linear or cyclic, and branched or unbranched. Substituents may have any structure as long as the resulting polysiloxanes are hydrophobic, are neither irritating, toxic nor otherwise harmful when applied to the oral cavity, and are compatible with the other components of the composition. Specific examples of suitable siloxane gums include polydimethylsiloxane, methylvinylsiloxane, polydimethylsiloxane/methylvinylsiloxane copolymer, poly (dimethylsiloxane, diphenyl, methyvinylsiloxane) copolymer and mixtures thereof. Silicone gums include those commercially available and marketed by General Electric. Silicone waxes include cosmetic waxes and silky waxes.

In some embodiments, the hydrophobic base comprises a silicone fluid (e.g., a polysiloxane Polysiloxane fluids useful herein for the hydrophobic base include those with a viscosity, at 25° C., of about 1 milliPascal-sec (mPa-s) to about 1000 mPa-s, or about 2 mPa-s to about 500 mPa-s, or about 20 mPa-s to about 400 mPa-s. Polysiloxane fluids for use herein can be linear or cyclic, and can be substituted with a wide variety of substituents. In certain embodiments, substituents include methyl, ethyl and phenyl substituents. Suitable polysiloxane fluids include linear polysiloxane polymers such as dimethicone and other low viscosity analogues of the polysiloxane materials, in certain embodiments having a viscosity, at 25° C., of 200 mPa-s or less and cyclomethicone, and other cyclic siloxanes having for example a viscosity, at 2.5° C., of 200 mPa-s or less. Other fluids include polysiloxane polyether copolymers and hydroxy terminated polydimethyl-siloxane fluid (e.g., Dow Corning ST-DIMETHICONOL™. 40, Dow Corning SGM 36. SGM3). Commercial examples of materials that are suitable for use herein include DC200 series fluids marketed by Dow-Corning Corporation and the AK Fluid series marketed by Wacker-Chemie GmbH, Munchen, Germany. High molecular silicone resins with a polysiloxane blend may also be used including powdered trimethylsiloxysilicate, for example, Dow Corning 593 fluid, Wacker Belsil TMS 803. Another suitable silicone fluid from Dow Corning is Q7-9210.

In some embodiments, the hydrophobic base comprises a silicone pressure sensitive adhesive (PSA). Such PSAs can be produced by condensing a silicone resin and an organosiloxane such as a polydiorganosiloxane. Such hydrophobic polymers are an elastomeric, tacky material, adhesion of which to dental enamel surfaces can be varied by altering the ratio of silicone resin to polydiorganosiloxane in the copolymer molecule. Such polymers are pressure sensitive hydrophobic polymers specifically designed for pharmaceutical use and are permeable to many drug compounds and find application for the transdermal application of various compounds. In some embodiments, the silicone polymers are the copolymer product of mixing a silanol terminated polydiorganosiloxane such as polydimethyl siloxane with a silanol-containing silicone resin whereby the silanol groups of the polydiorganosiloxane undergo a condensation reaction with the silanol groups of the silicone resin so that the polydiorganosiloxane is lightly crosslinked by the silicone resin (that is, the polydiorganosiloxane chains are bonded together through the resin molecules to give chain branching and entanglement and/or a small amount of network character) to form the silicone hydrophobic polymers. A catalyst, for example, an alkaline material, such as ammonia, ammonium hydroxide or ammonium carbonate, can be mixed with the silanol-terminated polydiorganosiloxane and the silicone resin to promote this crosslinking reaction. By copolymerizing the silicone resin with the silanol terminated polydiorganosiloxane, there results a polymer with self-adhering properties and the cohesive properties of a soft elastomer matrix characteristic of pressure sensitive polymers being distinguished from the hard, non-elastomeric properties of other silicone resins. In one embodiment, hydrophobic polymers used in the carrier are available from the Dow-Corning Company under the brand name BIO-PSA. The modification of a ratio of silicone resin to polydiorganosiloxane modifies the tackiness of the polymer. This ratio can be in the range of about 70:30 to about 50:50. For example, the BIO PSA silicone sold by Dow-Corning is available in three silicone resin to silicone polymer ratios namely, 65/35 (low tack), 60/40 (medium tack), 55/45 (high tack). Such a polyorganosiloxane PSA is available dissolved in either ethyl acetate solvent or dimethicone. Modifying the silicone resin to polydiorganosiloxane ratio of the PSA will modify the tackiness of the PSA. For example, the BIO PSA silicone adhesive sold by Dow-Corning is available in three silicone resin to silicone polymer ratios namely, 65/35 (low tack), 60/40 (medium tack), 55/45 (high tack) dissolved in either ethyl acetate solvent or dimethicone. A suitable silicone PSA is Silicone Adhesive 8-7016, commercially available from Dow Corning.

In some embodiments, the hydrophobic comprises a mixture of a silicone adhesive and a silicone gum, for example, PSA silicone and dimethicone.

In some embodiments the hydrophobic base is present at a concentration of 20 to 80%, by weight of the composition. In some embodiments, the hydrophobic base is present at a concentration of 40 to 80%, by weight of the composition. In some embodiments, the hydrophobic base is present at a concentration of 60 to 80%, by weight of the composition. In some embodiments, the hydrophobic component is present at a concentration of 60 to 70% or 70 to 80%, by weight of the composition. In some embodiments, the hydrophobic component is present at a concentration of about 60%, about 65%, about 70% or about 75%, by weight of the composition.

Suitable hydrophilic polymers include polyethylene glycols, block copolymers of ethylene oxide and propylene oxide, carboxymethylene polymers, N-vinyl heterocyclic polymers, and mixtures thereof. In dual-phase compositions, one or more of the same hydrophilic polymers may be present in both phases.

In some embodiments, the hydrophilic polymer comprises an N-vinyl heterocyclic polymer. The N-vinyl heterocyclic polymer is derived from a N-heterocyclic vinyl monomer, preferably comprising N-vinyl heterocyclic monomers having from 3 to 7 atoms in a heterocyclic ring, including a carbonyl carbon atom and a nitrogen heteroatom containing a vinyl group. Preferably the ring contains 5 or 6 atoms, comprises heteroatoms such as sulfur or oxygen, and may be substituted or unsubstituted. In some embodiments, the hydrophilic polymer comprises the polymers of specific N-vinyl heterocyclic monomers such as N-vinyl imides to form poly-N-vinyl polyimides, and N-vinyl lactams to form poly-N-vinyl polylactams, and mixtures thereof.

Suitable N-vinyl imides include: N-vinyl malonimide; N-vinyl succinimide; N-vinyl glutarimide; N-vinyl maleimide; N-vinyl β-methylglutarimide; N-vinyl α-amylsuccinimide; and N-vinyl adipimide. Suitable N-vinyl lactams include: N-vinyl peperidone; caprolactam; N-vinyl-3-methylpyrrolidinone or piperidone, or caprolactam; N-vinyl-4-methyl pyrrolidinone, or piperidone or caprolactam; N-vinyl-5-methylpyrrolidinone or piperidone; N-vinyl-3-ethyl pyrrolidinone; N-vinyl-4,5-dimethyl pyrrolidinone; N-vinyl-5,5-dimethyl pyrrolidinone; N-vinyl-3,3,5-trimethyl pyrrolidinone; N-vinyl-5-methyl-5-ethyl pyrrolidinone; N-vinyl-3,4,5-trimethyl-3-ethyl pyrrolidinone; N-vinyl-6-methyl-2-piperidone; N-vinyl-6-ethyl-2-piperidone; N-vinyl-3,5-dimethyl-2-piperidone; N-vinyl-4,4-dimethyl-2-piperidone; N-vinyl-7-methyl caprolactam; N-vinyl-7-ethyl caprolactam; N-vinyl-3,5-dimethyl caprolactam; N-vinyl-4,6-dimethyl caprolactam; N-vinyl-3,5,7-trimethyl caprolactam. Embodiments containing poly-N-vinyl polylactams, include but are not limited to, poly-N-vinyl pyrrolidone, poly-N-vinyl-2-piperidone, poly-N-vinyl-2-caprolactam, poly-N-vinyl-3-methyl-2-caprolacam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, and mixtures thereof. Preferably, the hydrophilic polymer comprises a polymer selected from the group consisting of poly-N-vinyl poly-2-pyrrolidone, poly-N-vinyl-poly-2-piperidone, poly-N-vinyl-poly-2-caprolactam and mixtures thereof.

In a preferred embodiment, the hydrophilic polymer comprises poly-N-vinyl-poly-2-pyrrolidone. The poly-N-vinyl-poly-2-pyrrolidone is also commonly known as polyvinylpyrrolidone or "PVP". PVP refers to a polymer containing vinylpyrrolidone (also referred to as N-vinyipyrrolidone, N-vinyl-2-pyrrolidione and N-vinyl-2-pyrrolidinone) as a monomeric unit. The monomeric unit, consists of a polar imide group, four non-polar methylene groups and a non-polar methane group. The polymers include soluble and insoluble homopolymeric PVPs. Copolymers containing PVP include vinylpyrrolidone/vinyl acetate (also known as Copolyvidone, Copolyvidonum or VP-VAC) and vinyl pyrrolidoneldimethylamino-ethylmethacrylate. Soluble PVP polymers among those useful herein are known in the art, including Povidone, Polyvidone, Polyvidonum, poly(N-vinyl-2-pyrrolidinone), poly (N-vinylbutyrolactam), poly(l-vinyl-2-pyrrolidone) and poly [1-(2-oxo-1 pyrrolidinyl)ethylene]. These PVP polymers are not substantially cross-linked.

In some embodiments, the hydrophilic polymer comprises an insoluble cross-linked homopolymer. Such polymers include crosslinked PVP (often referred to as cPVP, polyvinylpolypyrrolidone, or cross-povidone).

In some embodiments, the hydrophilic polymer comprises a mixture of soluble linear polymers and insoluble cross-linked polymers, for example, a mixture of linear PVP and cross-linked PVP.

In some embodiments, the hydrophilic polymer may comprise a polymer of ethylene oxide, also known as a polyethylene glycol, having the general formula $H-(OCH_2CH_2)_nOH$, wherein n represents the average number of oxyethylene groups. Polyethylene glycols available from Dow Chemical (Midland, Mich., U.S.A.) are designated by number such as 200, 300, 400, 600, 2000 which represents the approximate average molecular weight of the polymer. In some embodiments, the hydrophilic polymer may comprise a polyethylene glycol of average molecular weight 200 to 1000, e.g., 400 to 800. For example, the composition may comprise one or more of polyethylene glycols 400, 500, 600 and 800.

In some embodiments, the hydrophilic polymer comprises a block copolymer of ethylene oxide and propylene oxide of the formula (also called a polyethylene glycol/polypropylene glycol block copolymer, or PEG/PPG copolymer). In some embodiments, the block copolymer has the general formula (ethylene oxide)x(propylene oxide)y, wherein x is an integer from 80 to 150 and y is an integer from 30 to 80. For example, x may be from 100 to 130 and/or y may be from 30 to 80. In some embodiments, the ethylene oxide constituent comprises from 65 to 75% by weight, of the copolymer molecule and the copolymer has an average molecular weight of 2,000 to 15,000. In some embodiments, the average molecular weight of the block copolymer is from 5000 to 10,000. A particular block copolymer useful herein is Pluraflo L1220 (marketed by BASF, Mount Olive. N.J., U.S.A.), which has an average molecular weight of about 9,800, comprises about 65% by weight of the ethylene oxide block, and has a general formula wherein x is about 116 and y is about 66.

Other useful hydrophilic polymers carbomers such as carboxymethylene polymers such as acrylic acid polymers, and acrylic acid copolymers. Carboxypolymethylene is a slightly acidic vinyl polymer with active carboxyl groups. One such carboxypolymethylene is Carbopol® 974 marketed by Noveon, Inc. Cleveland, Ohio, U.S.A.

The viscosity of each phase of the composition of the invention is preferably greater than 1,000 centipoise (cPs)

and less than 900,000 cPs, in a more specific embodiment greater than 10,000 cPs and less than 100,000 cPs, in a more specific embodiment greater than 50,000 cPs and less than 900,000 cPs, and in an even more specific embodiment from between 200,000 cPs to 600,000 cPs.

In some embodiments, one or more buffering agents are present. The buffering agent or agents may be present in either the non-aqueous phase or the aqueous phase of a dual phase composition, or both phases. Examples of buffering agents include anhydrous carbonates such as sodium carbonate, sesquicarbonates, bicarbonates such as sodium bicarbonate, silicates, bisulfates, phosphates such as monopotassium phosphate and dipotassium phosphate, citrates, pyrophosphates (sodium and potassium salts), hydroxides such as sodium and potassium hydroxide, and combinations thereof. For a single phase composition, the amount of buffering agent should be effective to achieve a pH of about 5 to about 9, preferably about 6 to about 8, and more preferably about 7, when the composition is mixed with water. For the dual phase composition, the amount of buffering agent, considering both phases, should be effective to achieve the above pH range when the two combined phases are mixed with water. Typical amounts of buffering agent include 5% to 35%, e.g., 10% to 30%, or 15% to 25%, or 5% to 25%, or 10% to 25%, by weight of the each phase of the composition.

In some embodiments, one or more additional whitening agents are present to enhance the effectiveness of the peroxysulfate whitening agent. The additional whitening agent or agents may be present in either the non-aqueous phase or the aqueous phase of a dual phase composition, or both phases. Such additional whitening agents may include peroxides and hydroperoxides, such as hydrogen peroxide, peroxides of alkali and alkaline earth metals, organic peroxy compounds, peroxy acids, salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include urea peroxide, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as percarbonate, perphosphate, perborate and persilicate salts of alkali and alkaline earth metals such as lithium, potassium, sodium, magnesium, calcium and barium, and mixtures thereof. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, sodium, potassium, magnesium, calcium and barium. Non-peroxide whitening agents also include colorants, such as titanium dioxide and hydroxyapatite.

In some embodiments, the compositions of the present disclosure optionally comprise a thickener and/or gelling agent. The thickener or gelling agent or agents may be present in either the non-aqueous phase or the aqueous phase of a dual phase composition, or both phases. Examples of thickeners and gelling agents useful herein include inorganic thickening silicas such as: an amorphous silica, for example Zeodent® 165 (Huber Corporation); Irish moss; iota-carrageenan; carboxyvinyl polymers, laponite, cellulose ethers and salts of cellulose ethers (such as sodium carboxymethylcellulose, hydroxypropyl methylcellulose, hydroxyethyl methylcellulose, hydroxyethyl cellulose), natural gums such as gum karaya, xanthan gum, guar gum, gum arabic, and gum tragacanth, homopolymers of acrylic acid cross-linked with an alkyl ether of pentaerythritol or an alkyl ether of sucrose; carbomers, and combinations thereof. Such agents may be present in either or both phase in amounts from 0.1 to 15% by weight, or from 0.5 to 10% or 1 to 5% by weight of the composition.

In some embodiments, the compositions of the present disclosure optionally comprise a tartar control or anticalculus agent. The tartar control or anticalculus agent or agents may be present in either the non-aqueous phase or the aqueous phase of a dual phase composition, or both phases. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate (SHMP) and mixtures thereof. In a particular embodiment SHMP is used. The amount of stain prevention agent optionally present is from about 0.1% to about 10%, in another embodiment from about 2% to about 9%, and in another embodiment from about 5% to about 8%, or about 7%, by weight, of the composition.

In some embodiments, the compositions of the present disclosure optionally comprise one or more surfactants. Suitable surfactants are those that are reasonably stable and foam throughout a wide pH range. The surfactants may be present in either the non-aqueous phase or the aqueous phase of a dual phase composition, or both phases. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Nonionic surfactants that can be used in the compositions can broadly be defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from 8 to 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al. in U.S. Pat. No. 4,051,234. The present composition typically comprises one or more surfactants each at a level of from 0.25% to 12%, by weight of each phase of the composition, preferably from 0.5% to 8%, and most preferably from 1% to 6% or 2 to 4%, by weight of the composition, for example, about 2%.

Other optional additives may be included. These optional agents may be present in either the non-aqueous phase or the aqueous phase of a dual phase composition, or both phases. Among such optional additives, included are those provided in order to change appearance or aesthetic appeal, and/or to preserve the final product, and/or for taste/cosmetic appeal and/or as therapeutic and prophylactic ingredients for oral health, prevention or treatment of a condition or disorder of hard or soft tissue of the oral cavity, or the prevention or treatment of a physiological disorder or condition. These optional additives include sweeteners, flavoring agents and colorants.

Sweeteners include both natural and artificial sweeteners. Suitable sweeteners include water soluble sweetening agents such as monosaccharides, disaccharides and polysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, sucralose, cyclamate salts, dipeptide based sweeteners, such as L-aspartic acid derived sweeteners, including L-aspartyl-L-phenylalanine methyl ester (aspartame). In general, the effective amount of sweetener is utilized to provide the level of sweetness desired for a particular composition, which will vary with the sweetener selected. This amount will normally be from 0.001 to 5%, by weight. In some embodiments, the sweetener is sodium saccharin and is present at a concentration of about 0.01%, by weight.

Flavoring agents include, but are not limited to, natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavoring agents can be used individually or in admixture. Commonly used flavors include mints such as peppermint, artificial vanilla, cinnamon derivatives, and various fruit flavors, whether employed individually or in admixture. Generally, any flavoring agent or food additive, such as those described in Chemicals Used in Food Processing, publication 1274 by the National Academy of Sciences, pages 63-258, may be used. Typically, flavoring agents, if included, are present at a concentration of from 0.01 to 1%, by weight. In some embodiments, the flavoring agent may be present at a concentration of about 0.2%, by weight.

Colorants, such as dyes, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl)indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4{[4-(N-ethyl-p-sulfobenzylamino)-phenyl]-(3-hydroxy-2-sulfoniumphenyl)-methylene}-[1-(N-ethyl-N-p-sulfobenzyl)-DELTA-3,5-cycl-ohexadienimine], FD&C Blue No. 1 (disodium salt of dibenzyldiethyl-diamino-triphenylcarbinol trisulfonic acid anhydrite), FD&C Blue No. (sodium salt of disulfonic acid of indigotin) and mixtures thereof in various proportions. Typically, colorants if included are present in very small quantities.

In some embodiments, the aqueous phase of the composition may further comprise a humectant, such as glycerin, sorbitol or propylene glycol. In some embodiments, the aqueous phase comprises a humectant at a level of from 10 to 80% by weight, or 20 to 60% by weight of the aqueous phase, or 20 to 40%, or 40 to 80%, or about 60%.

All ingredients for use in the formulations described herein should be orally acceptable. By "orally acceptable" as the term is used herein is meant an ingredient which is present in the formulation as described in an amount and form which does not render the formulation unsafe, unpalatable, or otherwise unsuitable for use in the oral cavity.

In particular embodiments, the present disclosure provides the following oral care whitening compositions:

1.1 An oral care whitening composition comprising a non-aqueous phase comprising a peroxysulfate whitening agent, a hydrophobic base and at least one hydrophilic polymer.
1.2 Composition 1.1, wherein the composition further comprises an aqueous phase comprising at least one hydrophilic polymer.
1.3 Composition 1.1 or 1.2, wherein the non-aqueous phase is a gel.
1.4 Composition 1.3, wherein the aqueous phase is a gel.
1.5 Any preceding composition, wherein the non-aqueous phase is substantially anhydrous.
1.6 Any preceding composition, wherein the peroxysulfate whitening agent comprises a salt of peroxysulfuric acid, e.g., a sodium, potassium, calcium, barium, magnesium or peroxysulfate.
1.7 Any preceding composition, wherein the peroxysulfate whitening agent comprises potassium peroxymonosulfate.
1.8 Any preceding composition, wherein the peroxysulfate whitening agent comprises potassium peroxydisulfate.
1.9 Any preceding composition, wherein the peroxysulfate whitening agent is present in an effective amount to whiten the teeth, e.g, from 0.1 to 40 wt % of the composition, or 1 to 20 wt %, or 1 to 15 wt %, or 1 to 10 wt % or 1 to 5 wt %, or 5 to 10 wt %, or about 1%, or about 5% or about 10%.
1.10 Any preceding composition, wherein the hydrophobic base comprises at least one silicone compound selected from silicone polymers, silicone adhesives, silicone gums, silicone waxes, silicone elastomers, silicone fluids, silicone resins, silicone powders, and mixtures thereof.

1.11 Any preceding composition, wherein the hydrophobic base comprises one or more siloxane polymers, e.g., one or more polyorganosiloxanes such as polydimethylsiloxane.

1.12 Any preceding composition, wherein the hydrophobic base comprises a silicone gum (e.g., a polysiloxane gum), a silicone fluid (e.g., a polysiloxane fluid, e.g., a dimethicone), or a silicone pressure sensitive adhesive, or a combination thereof.

1.13 Any preceding composition, wherein the hydrophobic base comprises a silicone gum (e.g., a polysiloxane gum).

1.14 Any preceding composition, wherein the hydrophobic base comprises a silicone fluid (e.g., a polysiloxane fluid, e.g., a dimethicone)

1.15 Any preceding composition, wherein the hydrophobic base comprises a silicone pressure sensitive adhesive.

1.16 Any preceding composition, wherein the hydrophobic base is present at a concentration of 20 to 80%, by weight of the composition, e.g., 40 to 80%, or 60 to 80%, or 60 to 70%, or 70 to 80%, or about 60%, about 65%, about 70% or about 75%, by weight of the composition.

1.17 Any preceding composition, wherein the hydrophilic polymer of the non-aqueous phase and/or the hydrophilic polymer of the aqueous phase, if any, is selected from polyethylene glycols, block copolymers of ethylene oxide and propylene oxide, carboxymethylene polymers, N-vinyl heterocyclic polymers, and mixtures thereof.

1.18 Any preceding composition, wherein the hydrophilic polymer of the non-aqueous phase and/or the hydrophilic polymer of the aqueous phase, if any, comprises an N-vinyl heterocyclic polymer, e.g., polyvinylpyrrolidone.

1.19 Composition 1.18, wherein the polyvinylpyrrolidone is linear PVP or cross-linked PVP or a mixture thereof.

1.20 Any preceding composition, wherein the hydrophilic polymer of the non-aqueous phase and/or the hydrophilic polymer of the aqueous phase, if any, comprises a polyethylene glycol, e.g., a PEG of average molecular weight 200 to 1000, or 400 to 800, or one or more of polyethylene glycols 400, 500, 600 and 800.

1.21 Any preceding composition, wherein the hydrophilic polymer of the non-aqueous phase and/or the hydrophilic polymer of the aqueous phase, if any, comprises a block copolymer of ethylene oxide and propylene oxide, e.g., wherein the block copolymer has the general formula (ethylene oxide)x(propylene oxide)y, wherein x is an integer from 80 to 150 and y is an integer from 30 to 80.

1.2.2 Any preceding composition, wherein the hydrophilic polymer of the non-aqueous phase and/or the hydrophilic polymer of the aqueous phase, if any, comprises a block copolymer of ethylene oxide and propylene oxide, wherein the ethylene oxide constituent comprises from 65 to 75% by weight, of the copolymer, optionally about 65% by weight.

1.23 Any preceding composition, wherein the hydrophilic polymer of the non-aqueous phase and/or the hydrophilic polymer of the aqueous phase, if any, comprises a block copolymer of ethylene oxide and propylene oxide, wherein the average molecular weight of the copolymer is from 2,000 to 15,000, e.g., from 5000 to 10,000, e.g., about 9800.

1.24 Any preceding composition, wherein the hydrophilic polymer of the non-aqueous phase and/or the hydrophilic polymer of the aqueous phase, if any, comprises a block copolymer of ethylene oxide and propylene oxide, wherein the block copolymer has the general formula (ethylene oxide)x(propylene oxide)y, wherein x is an integer from 100 to 130 and y is an integer from 30 to 80, e.g., x is about 116 and y is about 66.

1.25 Any preceding composition, wherein the hydrophilic polymer of the non-aqueous phase and/or the hydrophilic polymer of the aqueous phase, if any, comprises a polycarboxymethylene polymer, e.g., a Carbopol.

1.26 Any preceding composition, wherein the viscosity of the non-aqueous phase is from 1,000 centipoise (cPs) to 900,000 cPs, e.g., from 10,000 cPs to 100,000 cPs, or from 50,000 cPs to 900,000 cPs, or from 200,000 cPs to 600,000 cPs.

1.27 Any preceding composition, wherein the non-aqueous phase and/or the hydrophilic polymer of the aqueous phase, if any, further comprises one or more buffering agents, for example, selected carbonates (e.g. sodium carbonate), sesquicarbonates, bicarbonates (e.g. sodium bicarbonate), silicates, bisulfates, phosphates (e.g. monopotassium phosphate and dipotassium phosphate), citrates, pyrophosphates (e.g. sodium and potassium pyrophosphate), hydroxides (e.g. sodium and potassium hydroxide), and combinations thereof.

1.28 Any preceding composition, wherein the non-aqueous phase and/or the hydrophilic polymer of the aqueous phase, if any, further comprises one or more additional whitening agents, e.g., selected from peroxides and hydroperoxides, such as hydrogen peroxide, peroxides of alkali and alkaline earth metals, organic peroxy compounds, peroxy acids, salts thereof.

1.29 Any preceding composition, wherein the non-aqueous phase and/or the hydrophilic polymer of the aqueous phase, if any, further comprises a tartar control or anti-calculus agent.

1.30 Any preceding composition, wherein the non-aqueous phase and/or the hydrophilic polymer of the aqueous phase, if any, further comprises a surfactant, e.g., an anionic, nonionic, amphoteric, zwitterionic, or cationic surfactant, or mixtures thereof.

1.31 Composition 1.30, wherein the non-aqueous phase and/or the hydrophilic polymer of the aqueous phase, if any, comprises sodium lauryl sulfate.

1.32 Any preceding composition, wherein the aqueous phase, if any, comprises a humectant, e.g., glycerin, sorbitol or propylene glycol, optionally in an amount of from 10 to 80% by weight of the phase, or 20 to 80%, or 20 to 60%, or 40 to 80%, or about 60%.

In another aspect, the present disclosure provides a method for whitening a tooth comprising applying any foregoing composition, e.g., composition 1.1 to 1.32, to a tooth of a mammal (e.g., a human). In some embodiments, the composition is applied using a pen. In some embodiments, the composition is maintained on the surface of the tooth for a period of time, e.g., from 1 minute to 8 hours, or 5 minutes to 4 hours, or 10 minutes to 120 minutes, or 15 minutes to 60 minutes, or 20 minutes to 45 minutes, or about 30 minutes.

In another aspect, the present disclosure provides use of any foregoing composition, e.g., Composition 1.1 to 1.32, for whitening the teeth of a mammal (e.g., a human). In some embodiments, the composition is applied using a pen. In some embodiments, the composition is maintained on the surface of the tooth for a period of time, e.g., from 1 minute to 8 hours, or 5 minutes to 4 hours, or 10 minutes to 120 minutes, or 15 minutes to 60 minutes, or 20 minutes to 45 minutes, or about 30 minutes.

In some embodiments, the compositions of the present invention can be prepared by adding and mixing the ingredients of the composition in a suitable vessel such as a stainless steel tank provided with a mixer in the preparation of the whitening compositions described herein, the ingredients are advantageously added to the mixer in the following order: hydrophobic component, whitening agent, hydrophilic polymer, and any desired flavoring or sweetener. The ingredients are then mixed to form a homogeneous dispersion/solution.

In some embodiments, the compositions of the present invention are applied to the tooth of a subject, by manual application, such as by painting the teeth with a soft applicator brush in the same manner as application of nail polish to a finger nail and without the intervention of a dentist or technological operations. Application by the user, leaves a coating of the thick liquid suspension on the teeth. Contact with saliva promotes the slow release of active whitening species (e.g., oxygen) the peroxysulfate compound, and permits efficient whitening agent action at the surface of the tooth.

As used herein, "whitening" refers to a change in visual appearance of a tooth, preferably such that the tooth has a brighter shade. Increase in whiteness of a dental surface can be observed visually, for example with the aid of color comparison charts or gauges, or measured by colorimetry, using any suitable instrument such as a Minolta Chromameter, e.g., model CR-400 (Minolta Corp., Ramsey, N.J.). The instrument can be programmed, for example, to measure Hunter Lab values or L*a*b* values according to the standard established by the International Committee of Illumination (CIE). The L*a*b* system provides a numerical representation of three-dimensional color space where L* represents a lightness axis, a* represents a red-green axis and b* represents a yellow-blue axis. The L* and b* axes are typically of greatest applicability to measurement of tooth whiteness. Increase in whiteness can be computed from differences in L*, a* and b* values before and after treatment, or between untreated and treated surfaces.

As used herein, "tooth" or "teeth" refers to natural mammalian teeth, dentures, dental plates, fillings, caps, crowns, bridges, dental implants, and the like, and any other hard surfaced dental prosthesis either permanently or temporarily fixed within the oral cavity.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Embodiments of the present invention are further described in the following examples. The examples are merely illustrative and do not in any way limit the scope of the invention as described and claimed.

EXAMPLES

Example 1

An experimental program is conducted to develop an improved hydrophobic oral gel composition comprising potassium monoperoxysulfate (MPS) which provides as good or better whitening efficacy than a comparative hydrogen peroxide-based composition, but without the poor rheological properties of a comparative hydrophobic MPS composition. Table 1 below shows a series of experimental compositions, as well as a hydrophobic MPS Comparative Composition 1 and hydrogen peroxide Comparative Compositions 2 and 3.

TABLE 1

| | (Weight %) | | | | | | | | |
|---|---|---|---|---|---|---|---|---|---|
| | Comparative Compositions | | | Exemplary Compositions | | | | | |
| Ingredient | 1 | 2 | 3 | A | B | C | D | E | X |
| Silicone adhesive | 30.0 | 30.0 | | 30.0 | 30.0 | 30.0 | 30.0 | 30.0 | |
| Silicone fluid (dimethicone) | 15.55 | 16.15 | | 15.7 | 38.7 | 29.7 | 15.7 | 29.7 | |
| Plasticized hydrocarbon base | 35.0 | 35.0 | | 8.0 | | | 7.00 | | |
| PVP-H$_2$O$_2$ complex | | 0.55 (0.1% H$_2$O$_2$) | | | | | | | |
| 35% Aq. H$_2$O$_2$ | | | 0.29 | | | | | | |
| MPS | 1.00 | | | 1.00 | 1.00 | 10.00 | 2.00 | 10.00 | |
| PEG/PPG 116/66 copolymer | | | | 10.00 | 10.00 | 10.00 | 10.00 | 10.00 | |
| Cross-linked PVP | 18.15 | 18.0 | | 29.7 | 16.2 | 16.2 | 29.7 | 16.2 | |
| Linear PVP | | | 2.0 | 3.3 | 1.8 | 1.8 | 3.3 | 1.8 | |
| Carbopol 974 | | | 5.3 | | | | | | 10.0 |
| Sodium lauryl sulfate | | | | 2.00 | 2.00 | 2.00 | 2.00 | 2.00 | |
| Sodium saccharin | 0.3 | 0.3 | 0.4 | 0.3 | 0.3 | 0.3 | 0.3 | 0.3 | |
| Glycerin | | 60.9 | | | | | | | |
| 50% Aq. NaOH | | 4.5 | | | | | | | 6.0 |
| NaF | | 0.25 | | | | | | | |
| KNO$_3$ | | 0.5 | | | | | | | |

TABLE 1-continued

| | (Weight %) | | | | | | | | |
|---|---|---|---|---|---|---|---|---|---|
| | Comparative Compositions | | | Exemplary Compositions | | | | | |
| Ingredient | 1 | 2 | 3 | A | B | C | D | E | X |
| Disodium EDTA | | | 0.02 | | | | | | |
| Flavor | | | 0.6 | | | | | | |
| Water | | | 25.2 | | | | | | 84.0 |

Table 1 also shows Exemplary Compositions A-E and X. Exemplary Compositions A, B and C are single-phase compositions, Exemplary Compositions D and E are the non-aqueous phase of a dual-phase composition, wherein Exemplary Composition X is the aqueous phase for each of those compositions. In practice, the two phases of these dual phase compositions are combined in a 1:1 ratio.

Comparative Composition 1 is a single-phase whitening composition with NIPS as its whitening agent which serves as the baseline composition. It is desired to improve the rheological properties of this baseline composition, while also improving the whitening efficacy to a level equal to or exceeding that of the hydrogen peroxide-based Comparative Compositions 2 and 3. A series of 28 compositions derived from baseline Comparative Composition Composition 1 are prepared each containing varying amounts of linear PVP, cross-linked PVP, sodium lauryl sulfate, and PEG 116/66 copolymer. Each of the 28 compositions has the same or similar amounts of silicone fluid, dimethicone, NIPS and sodium saccharin as Comparative Composition 1. These 28 compositions are compared in a fast lissamine green dye bleaching experiment for bleaching efficacy.

Briefly, in the lissamine green dye experiment, 0.25 g of the gel composition is smeared into a scintillation vial containing a 10% lissamine green dye solution in pH 7.4 phosphate buffer. The solution is mixed at 200-250 rpm, and every 15 minutes a 0.1 mL aliquot of the solution is removed and its absorbance at 610 nm measured in a spectrophotometer. Lissamine green dye absorbs strongly at 610 nm, and the whitening agent gradually destroys the dye, lowering the level of absorbance.

Exemplary Composition A is found to have the most superior bleaching performance of the 28 compositions compared, and it is a significantly stronger bleaching gel than Comparative Composition 1, as shown below:

TABLE 2

| | Absorbance at 610 nm | | | | | | |
|---|---|---|---|---|---|---|---|
| | 0 min | 15 min | 30 min | 45 min | 60 min | 75 min | 90 min |
| Comparative Composition 1 | 0.288 | 0.260 | 0.251 | 0.236 | 0.225 | 0.201 | 0.190 |
| Exemplary Composition A | 0.288 | 0.168 | 0.107 | 0.075 | 0.058 | 0.026 | 0.028 |

Example 2

The next step is to improve the rheological parameters of the whitening composition. It is found that while Exemplary Composition A has excellent bleaching capacity, it is too viscous for easy consumer use. In order to improve the viscosity, the proportions of hydrophobic base ingredients, hydrophilic polymers and surfactant was adjusted. It is found that Exemplary. Compositions B and C both achieve desired viscosity. Exemplary Compositions B and C are then compared to hydrogen peroxide based Comparative Composition 2 for whitening efficacy.

Bovine enamel blocks are obtained freshly stained using an established staining protocol (Indiana University, Indianapolis, Ind.). The stained bovine incisors are first brushed with a toothbrush and commercial toothpaste for 30 minutes, then the teeth or sorted into matched groups based on initial L*, a* and b* values measured on a Minolta CR-321 chromometer (CIELAB). The L, a, b values are measured four times at slightly differing locations on the surface of the bovine enamel blocks, Each group of teeth is subjected to the same treatment cycle fourteen times. Each treatment cycle consists of the following steps:
 (1) Approximately 50 mg of gel composition is spread evenly across the teeth.
 (2) The teeth are inverted and submerged in a trough through which pH 7.4 buffer flows at a rate of 2.5 mL/min for 15 minutes (this imitates the action of saliva)
 (3) The teeth are removed, and any remaining gel is gently cleaned off with a laboratory wipe
 (4) The teeth are inverted and replaced in the trough with the running buffer for an additional 15 minutes (to rehydrate the teeth), followed by measurements.

Whitening efficacy is calculated as the parameter $\Delta W$, and the results are shown below. It is found that Exemplary Composition B has comparable whitening efficacy to Comparative Composition 2, while Exemplary Composition C has significantly superior efficacy.

TABLE 3

| $\Delta W$ after cycles: | 2 | 4 | 6 | 8 | 10 | 12 | 14 |
|---|---|---|---|---|---|---|---|
| Comparative Composition 2 | −0.55 | −0.78 | −1.12 | −0.95 | −1.14 | −1.19 | −1.30 |
| Exemplary Composition B | −0.50 | −1.06 | −0.97 | −0.94 | −0.91 | −0.92 | −1.71 |
| Exemplary Composition C | −0.98 | −0.93 | −1.60 | −1.67 | −1.69 | −2.09 | −2.71 |

Example 3

Dual phase whitening compositions are then evaluated to optimize whitening efficacy and improve stability. Comparative Composition 3 is compared to the dual phase formulations D+X and E+X. A similar whitening efficacy experiment is conducted as in Example 2, except that the four steps in each cycle are as follows:
 (1) Approximately 200 mg of gel composition 3, or 200 mg of a 1:1 mixture of gel composition D and X or E and X, is spread evenly across the teeth.
 (2) The teeth are exposed to air for 30 minutes.

(3) The teeth are cleaned of any remaining gel with a laboratory wipe, and are then soaked in artificial saliva for 10 minutes (4) The teeth are dried then measurements are taken.

It should be noted that due to the 1:1 mixing of Exemplary Compositions D or E with Composition X, the effective amount of MPS in the two tests are 2 wt % and 5 wt %, respectively, half of the formulated amount of Exemplary Compositions D and E, respectively. The results show that both Exemplary Compositions D+X and FHA show significantly improved whitening efficacy compared to the hydrogen peroxide Comparative Composition 3. In addition, it should be noted that these results are significantly better than the single-phase Exemplary Compositions B and C, shown in Example 2.

TABLE 4

| ΔW after cycles: | 2 | 4 | 6 | 8 | 10 | 12 | 14 |
|---|---|---|---|---|---|---|---|
| Comparative Composition 3 | −1.55 | −2.18 | −2.16 | −1.61 | −1.67 | −1.66 | −1.60 |
| Exemplary Compositions D + X (1:1) | −4.35 | −6.04 | −7.00 | −6.19 | −6.93 | −6.62 | −7.47 |
| Exemplary Compositions E + X (1:1) | −7.15 | −8.64 | −9.85 | −9.15 | −9.89 | −10.11 | −10.39 |

The invention claimed is:

1. An oral care whitening composition comprising a non-aqueous phase comprising:
   a peroxysulfate whitening agent comprising potassium peroxymonosulfate;
   a hydrophobic base comprising a silicone adhesive and a silicone polymer present in a weight ratio ranging from about 70:30 to about 50:50, wherein the hydrophobic base is present at a concentration of 20 to 80%, by weight of the composition; and
   at least one hydrophilic polymer comprising:
   a block copolymer of ethylene oxide and propylene oxide, wherein the ethylene oxide constituent comprises from 65% to 75% by weight of the copolymer;
   a mixture of soluble linear polymers and insoluble cross-linked polymers, selected from a mixture of linear polyvinylpolypyrrolidone (PVP) and cross-linked PVP; and
   wherein the non-aqueous phase is substantially anhydrous.

2. The composition of claim 1, wherein the composition further comprises an aqueous phase comprising at least one hydrophilic polymer.

3. The composition of claim 1, wherein the non-aqueous phase is a gel.

4. The composition of claim 2, wherein the aqueous phase is a gel.

5. The composition of claim 1, wherein the composition is a single phase substantially anhydrous composition.

6. The composition of claim 1, wherein the potassium peroxymonosulfate whitening agent is present in an effective amount to whiten the teeth.

7. The composition of claim 1, wherein the hydrophobic base comprises at least one silicone compound selected from silicone polymers, silicone adhesives, silicone gums, silicone waxes, silicone elastomers, silicone fluids, silicone resins, silicone powders, and mixtures thereof.

8. The composition of claim 1, wherein the hydrophobic base comprises one or more siloxane polymers.

9. The composition of claim 1, wherein the hydrophobic base comprises a silicone gum, a silicone fluid, or a silicone pressure sensitive adhesive, or a combination thereof.

10. The composition of claim 2, wherein the hydrophilic polymer of the non-aqueous phase and/or the hydrophilic polymer of the aqueous phase, if any, comprises a block copolymer of ethylene oxide and propylene oxide.

11. The composition of claim 2, wherein the hydrophilic polymer of the non-aqueous phase and/or the hydrophilic polymer of the aqueous phase, if any, comprises a polycarboxymethylene polymer.

12. The composition of claim 2, wherein the non-aqueous phase and/or the aqueous phase, if any, further comprises one or more buffering agents, selected from carbonates, sesquicarbonates, bicarbonates, silicates, bisulfates, phosphates, citrates, pyrophosphates, hydroxides, and combinations thereof.

13. The composition of claim 2, wherein the non-aqueous phase and/or the aqueous phase, if any, further comprises a surfactant.

14. The composition of claim 13, wherein the non-aqueous phase and/or the aqueous phase, if any, comprises sodium lauryl sulfate.

15. The composition of claim 1, wherein the composition consists of two phases, a first non-aqueous and substantially anhydrous phase comprising a peroxysulfate whitening agent, a hydrophobic base and at least one hydrophilic polymer, and a second aqueous phase comprising at least one hydrophilic polymer, and wherein the second phase does not comprise a whitening agent.

* * * * *

UNITED STATES PATENT AND TRADEMARK OFFICE
CERTIFICATE OF CORRECTION

PATENT NO. : 10,709,646 B2
APPLICATION NO. : 14/972649
DATED : July 14, 2020
INVENTOR(S) : Kyle Robbins et al.

It is certified that error appears in the above-identified patent and that said Letters Patent is hereby corrected as shown below:

In the Specification

In Column 2, Line 67, delete "0.11" and insert -- 0.1 --, therefor.

In Column 3, Line 61, after "a polysiloxane", insert -- fluid). --.

In Column 4, Line 7, delete "2.5°" and insert -- 25° --, therefor.

In Column 5, Line 43, before "caprolactam;", insert -- N-vinyl --.

In Column 6, Lines 5-6, delete "N-vinyipyrrolidone," and insert -- N-vinylpyrrolidone, --, therefor.

In Column 6, Lines 12-13, delete "pyrrolidoneldimethylamino" and insert -- pyrrolidone/dimethylamino --, therefor.

In Column 10, Line 14, delete "(3" and insert -- (4 --, therefor.

In Column 10, Line 19, after "Blue No.", insert -- 2 --.

In Column 13, Line 1, delete "mixer in" and insert -- mixer. In --, therefor.

In Column 15, Line 20, delete "NIPS" and insert -- MPS --, therefor.

In Column 15, Line 30, delete "NIPS" and insert -- MPS --, therefor.

In Column 17, Line 10, delete "FHA" and insert -- E+X --, therefor.

Signed and Sealed this
Twenty-second Day of September, 2020

Andrei Iancu
*Director of the United States Patent and Trademark Office*